United States Patent [19]

Rijkers et al.

[11] Patent Number: 5,733,883
[45] Date of Patent: Mar. 31, 1998

[54] CRYSTALLIZATION OF α-L-ASPARTYL-L-PHENYLALANINE METHYL ESTER FROM AQUEOUS SOLUTION

[75] Inventors: Marinus P. W. M. Rijkers, Elsloo; Alexander P. M. Vrinzen, Meerssen, both of Netherlands

[73] Assignee: Holland Sweetener Company V.O.F., Maastricht, Netherlands

[21] Appl. No.: 672,924

[22] Filed: Jun. 28, 1996

[30] Foreign Application Priority Data

Jun. 30, 1995 [EP] European Pat. Off. .............. 95201794

[51] Int. Cl.⁶ .......................... A61K 38/00; C07C 229/00
[52] U.S. Cl. ................................... 514/19; 560/41
[58] Field of Search ........................ 514/19; 560/41

[56] References Cited

U.S. PATENT DOCUMENTS 4,962,222   10/1990   Mita et al. .................. 560/41
5,298,648   3/1994    Ebisawa et al. ............. 560/41

FOREIGN PATENT DOCUMENTS 394 854 B   7/1992    Austria .
512 435     11/1992   European Pat. Off. .

OTHER PUBLICATIONS

Hatada et al, J. Amer. Chem. Soc. 107 4279–82 (1985).

*Primary Examiner*—Cecilia J. Tsang
*Assistant Examiner*—Bennett Celsa
*Attorney, Agent, or Firm*—Cushman Darby & Cushman IP Group of Pillsbury Madison & Sutro LLP

[57] ABSTRACT

Improved method for crystallization of α-L-aspartyl-L-phenylalanine methyl ester (aspartame) from an aqueous solution by conductive cooling while avoiding turbulence in the crystallizing system wherein crystallization is carried out with cooling to a temperature level not lower than 10° C. in the presence of at least 0.1% by weight of a $C_{3-8}$ ketone, the amount of ketone and the temperature level being chosen for each individual ketone so that a homogeneous solvent system is present at the start of crystallization and an open drainable network of aspartame crystals is obtained.

18 Claims, No Drawings

CRYSTALLIZATION OF α-L-ASPARTYL-L-PHENYLALANINE METHYL ESTER FROM AQUEOUS SOLUTION

BACKGROUND TO THE INVENTION

1. Field of the Invention

The invention relates to a method for the crystallization of α-L-aspartyl-L-phenylalanine methyl ester (hereinafter also referred to as aspartame or "APM") from an aqueous solution by conductive cooling while avoiding turbulence in the crystallizing system.

2. Description of the Related Art

Aspartame, the α-dipeptide ester L-aspartyl-L-phenylalanine methyl ester ("APM"), is an important synthetic low-calorie sweetening agent which is about 200 times as sweet as sugar and has an exceptionally good taste pattern without, for instance, a bitter aftertaste. The sweetener is used as such in a wide range of products such as soft drinks, sweets, table-top sweeteners, pharmaceutical products and the like.

Aspartame can be prepared by various known routes. There exist, for instance, routes whereby (N-protected) L-aspartic acid or the anhydride thereof and (L-)phenylalanine or the methyl ester thereof are chemically coupled, the protecting group optionally being removed later and APM being obtained by esterification if still necessary. Examples of such processes are disclosed in, for instance, U.S. Pat. No. 3,786,039. In processes for the chemical coupling of aspartame usually relatively large amounts of β-APM are formed as a side-product, and working-up of the desired α-APM often occurs through formation of e.g. the APM.HCi-salt and neutralization crystallization. Such methods inevitably lead to production of large amounts of salt.

There also exist enzymatic processes for the production of APM whereby, for instance, N-protected L-aspartic acid and (DL-)-phenylalanine methyl ester are selectively coupled to form the LL-α-dipeptide derivative and are subsequently converted to APM. Such a process is described in, for instance, U.S. Pat. No. 4,116,768.

In any commercial APM production process one of the final process steps is to obtain APM in crystalline form from the solvent in which it is present and wherein also other reaction (by-)products and/or decomposition products occur. Usually the solvent is an aqueous solvent, that is water or a mixed solvent of water and up to about 25% (wt.) of a water-miscible organic solvent, in particular a lower alcohol of one to three carbon atoms. The term "aqueous" as used herein will therefore specifically mean "water, or water containing up to about 25% (wt.) of a $C_{1-3}$ alcohol".

A method for crystallizing APM from aqueous solutions is described in EP-A-91787 (hereinafter also referred to as '787). According to that method APM is crystallized, at least for the major part of crystallization, using conductive heat transfer for cooling without effecting forced flow, i.e. under conditions where turbulence in the aqueous system is avoided. This method requires special equipment and leads, with appropriate cooling, to the formation of a sherbet-like pseudo-solid phase when starting from aqueous solutions of APM having an APM concentration of about 1% by weight or higher. Such a pseudo-solid phase always occurs at APM crystal concentrations of 1% by weight or higher after crystallization.

This can easily be demonstrated when (a hot) aqueous solution of APM (APM content of 1 wt. % or more) is crystallized in a beaker by allowing the solution to stand, in a refrigerator or even at ambient temperature, so that the APM crystallizes. Upon turning the beaker upside-down after crystallization it can be seen that all of the solvent remains in the pseudo-solid phase and cannot be drained therefrom without destroying this phase.

The formation of a pseudo-solid phase makes this static crystallization method rather unfavourable for industrial application. In particular, it does not allow crystallization, solid-liquid separation, crystal washing and drying to be performed in one vessel. Moreover, dewatering of the crystals thus obtained is still believed to be unsatisfactory; for instance, it can only be achieved to about 30–35% by centrifuging at 800 G. These are substantial disadvantages of this prior art method.

Accordingly, it is an object of the present invention to provide an improved method for the crystallization of APM from an aqueous solution by conductive cooling while avoiding turbulence in the crystallizing system which offers possibilities for performing crystallization, solid-liquid separation, crystal washing and drying in one vessel. It is a further object of the present method to provide APM crystals which have an improved solid-liquid behaviour in centrifuging.

SUMMARY OF THE INVENTION

These objects are achieved in that the method for crystallization of α-L-aspartyl-L-phenylalanine methyl ester from an aqueous solution by conductive cooling with avoiding of turbulence in the crystallizing system is carried out with cooling to a temperature level not lower than 10° C. in the presence of at least 0.1% by weight, referred to the total crystallizing system, of a ketone chosen from the group of $C_{3-8}$ ketones, the amount of ketone and the temperature level being chosen for each individual ketone so that a homogeneous solvent system is present at the start of crystallization and an open drainable network of α-L-aspartyl-L-phenylalanine methyl ester crystals is obtained.

This method provides an improved and elegant way of crystallizing APM by cooling from its aqueous solutions, offering the advantages of static crystallization of APM with regard to crystal properties to the same extent or even better, while presenting additional advantages with respect to industrial application of the static crystallization process for APM, in particular, in that it is now possible to perform crystallization, solid-liquid separation, crystal washing and drying of APM in one, though specially dedicated, vessel, and in that improved solid-liquid separation can be achieved in centrifuging.

The present invention therefore relates to an improved method for the crystallization of APM from an aqueous solution by conductive cooling while avoiding turbulence in the crystallizing system wherein crystallization is carried out with cooling to a temperature level not lower than 10° C. in the presence of at least 0.1% by weight, referred to the total crystallizing system, of a ketone chosen from the group of $C_{3-8}$ ketones, the amount of ketone and the temperature level being chosen for each individual ketone so that a homogeneous solvent system is present at the start of crystallization and an open drainable network of APM crystals is obtained.

The term "open drainable network" as used herein refers to the overall structure of the crystalline aspartame product obtained according to the present method. It relates to a novel aspartame product and properties thereof, which have not been described before. In aspartame crystallization methods of the prior art either a so-called "sherbet-like pseudo-solid phase" is formed (which is not drainable at all as described above); or a slurry of crystals is obtained from which on filtering, centrifuging or the like indeed substantial amounts of mother liquor can be separated, but the crystal mass then turns into a more or less compacted crystal cake. The open drainable network according to the present invention, in contrast, can be drained (i.e. a large part, in particular more than 30% by weight, of the mother liquor can be removed from it purely by gravitational force, and even a substantially higher percentage can be removed if an inert gas is passed -at reduced pressure, atmospheric pressure, or even at a higher pressure, as appropriate- through the resulting crystal structure) while maintaining its "apparent overall crystal volume": the resulting (that is after draining) network of crystalline product has a very open structure, which structure can be used with advantage in drying the product by passing an inert gas of elevated temperature, generally in the range of 60°–100° C., through the product without disturbing the overall structure and apparent overall crystal volume thereof. This is attributed to the specific method of crystallization according to the present invention. Of course, instead of passing an inert gas through the network of crystalline product obtained after draining, other drying methods can be used, for instance introducing heat into the system under conditions of reduced pressure (vacuum) or microwave drying, or the like.

Additional advantages of the present method have been found in that the dissolution time of the crystalline product is significantly improved, and in that the electrostatic properties thereof are very much improved, as can for instance be seen in the so-called "spoon-test" (details of which are described in the experimental part hereof). The latter may be an advantage for some specific applications of aspartame, such as its use in chewing gum.

It is noted that in the prior art various crystallizations of aspartame, particularly with the aim of preparing large single crystals (for X-ray crystal structure determination or the like), have been described which take place in the presence of specific ketones and other organic and/or inorganic compounds. In none of these methods however the occurrence of an "open drainable network" has been observed and generally the methods resulted in extremely fine needles or fibres of aspartame crystals.

First of all reference is made here to an article by Hatada et al. (J. Am. Chem. Soc., 1985, p.4279–4282) who have succeeded, at ml-scale and allowing crystal growth for two weeks, in preparing large aspartame crystals, suitable for X-ray crystallographic studies, only from a specific quaternary solvent system (water, ethanol, acetone and dimethylsulphoxide); other, binary and ternary solvent systems appeared not to be suitable for preparing suitable crystals.

Further, the presence of organic co-solvents, in particular lower alcohols, also has been proposed for increasing the solubility of aspartame, and thus, upon cooling, increasing the aspartame crystal yield; or they have been proposed for improving the physical properties of the crystallization mixture. In AT-8601597-A (published 15 Dec., 1991) a rather complicated method for the preparation of aspartame is described; in part c) of the experimental part thereof incidentally crystallization of aspartame is shown in the presence of acetone; however, in that method a suspension of the aspartame hydrochloric acid salt in water/acetone is neutralized to a pH of 4.7 to form a suspension of aspartame which is kept for 12 hours while being cooled in an ice-bath. The crystal properties of this aspartame are rather poor, and during the process no "open, drainable network" of aspartame crystals is observed. "Crystallization in the presence of a ketone . . ." as used herein means that the ketone should be present before crystallization starts. This can be achieved either by starting from a hot solution of aspartame in a mixed solvent of water, optionally containing up to about 25% (wt.) of a $C_{1-3}$ alcohol, and the ketone chosen in the suitable amount, or by adding the ketone without causing substantial turbulence in the aspartame solution before nucleation starts and the first crystals of aspartame are formed. Of course, additional amounts of the ketone may be carefully added during crystallization so as not to effect substantial turbulence. It is, however, preferred for the total amount of ketone to be used to be present before crystallization starts and that the solvent system is homogeneous.

Ketones that are suitable for use in the method of the present invention are chosen from the group of $C_{3-8}$ ketones. In general these ketones have a solubility of at least 1 gram per 1000 grams of water at ambient temperature and are capable of forming homogeneous solvent mixtures with aqueous APM solutions if the amount of ketone is more than 0.1% by weight, referred to the total crystallizing system. The crystallizing system is defined herein as the total amount of solution (or -during crystallization-slurry) from which (or wherein) crystallization takes place, that is the total amount of solvent, APM and any other substances present.

This group consists of, inter alia, 2-propanone (acetone), 2-butanone, methylethylketone (MEK), 2-pentanone, 3-pentanone, methyl-isopropylketone, 2-hexanone, 3-hexanone, ethyl-isopropylketone, methyl-sec.butylketone, methyl-isobutylketone (MIBK), methyl-tert.butylketone, methyl-isopentylketone, methyl-tert.pentylketone, methyl-neopentylketone, ethyl-sec.butylketone, ethyl-isobutylketone, ethyl-tert.butylketone, 2-heptanone, 3-heptanone, 4-heptanone, di-isopropylketone, ethyl-isopentylketone, ethyl-tert.pentylketone, ethyl-neopentylketone, and various $C_8$ ketones. Cyclic ketones, for instance, cyclopentanone and cyclohexanone, as well as diketones, for example, 2,4-pentadione ("acac"), 2,5-hexadione, 1,4-cyclohexadione, 1,3-cyclohexadione, and unsaturated ketones, for instance, cyclopentenone, 3-cyclohexenone, and 4-octen-2-one, or mixtures thereof, are also suitable in the context of the present invention. The ketones that are suitable for use may also contain one or more other substituents, for instance, hydroxy, methoxy or halogen groups.

In particular adstone, MEK, (MIBK), and 2,5-hexanedione are suitable, acetone and MIBK being extremely suitable, because of their availability and ease of handling, and because the "open drainable networks" obtained are of very good quality. MIBK is most preferred because advantageous results are obtained even at very low levels of MIBK in the crystallizing system, more particularly at levels of about 0.1 to 2.0 weight percent. When using acetone preferably somewhat larger amounts of acetone, of about 1.0 even up to 20.0 weight percent in the crystallizing system, are used. The skilled in the art can easily determine what amounts of ketone yield the best results.

It is most surprising that the favourable "open drainable networks" of aspartame are obtained according to the method of the present invention. If, for instance, crystallization analogous to the present method is carried out from an APM solution in 75/25 water/methanol and no ketone is present during the crystallization, a non-drainable sherbet is formed. The use of aldehydes, esters, etc. instead of the ketone gives poor results; in case aldehydes are used it should be noted that crystallization indeed takes place; however, the crystals formed are crystals of the Schiff base of aspartame and the aldehyde instead of aspartame crystals.

As explained above the term aqueous solvent refers to water or to a mixed solvent of water and up to about 25% (wt.) of a water-miscible organic solvent, for instance a $C_{1-3}$ alcohol. Moreover, the presence of a lower alcohol may be advantageous in further process steps, such as in further treatment of the slurry, for instance by solvent removal under vacuum. The main advantage of using mixed solvents, however, is that higher concentrations of (dissolved) APM can be achieved in the starting solution.

For achieving good results the temperature of the hot aqueous (starting) solution of APM should preferably be at least 40° C. and the concentration of APM therein at least 2.5% by weight. If the temperature of the hot aqueous solution is lower than 40° C. the crystallization yield will become too low; also, if the concentration of APM therein is too low, unfavourable results will be obtained in respect of the quality of the open, drainable network finally obtained, or even very poor crystal properties of the needle-like crystals obtained will be found (see e.g. J. Chem. Biotech, 43, 71–82 (1988)). If the APM concentration in the starting solution is too high, drainability is lowered significantly. This, however, depends on the composition of the starting solution. In general drainability remains good up to an APM concentration of 7%.

The pH of the aqueous (starting) solution of APM is not very critical, and should preferably be in the range of 3.5 to 6.5, more preferably near the isoelectric point of APM, that is at a pH of 5.2. It is noted that the value of the pH is precisely defined for a solution in water alone, and is less precisely defined in the case where one or more co-solvents are present.

Advantageously cooling takes place to a temperature level of about 15° to 30° C., but not lower than 10° C. Preferably cooling is performed by indirect cooling as this gives the least turbulence in the system. Indirect cooling as used here is meant to refer to cooling at heat exchange surface areas formed by part or all of the walls of the crystallizing equipment; preferably a vessel is used, most preferably a tubular vessel, containing the aqueous APM solution with the ketone. It will be obvious that other types of equipment may also be used; for instance a cooling belt crystallizer can be used having a zone for crystallizing and further zones for draining and/or filtering and for washing the crystal structure formed and optionally passing an inert gas through the crystalline product. Also, vacuum may be applied during this process.

The equipment or vessel where crystallization takes place preferably is designed so that a sufficiently large cooling/heat transfer area, for instance walls and/or internals, is provided; there should also be means for retaining the open drainable network in the equipment or vessel while draining; optionally, means for passing an inert gas through the crystal network may be provided and/or means for drying and for destroying the open drainable network after the draining and optional further stages.

In particular, when using a vessel, an embodiment is preferred wherein cooling internals, if present, can be removed from the crystal mass without any problem due to scaling, and wherein the means for retaining the open drainable network in the vessel can be removed before emptying the vessel.

The temperature of the coolant used for cooling the crystallizing system in the equipment will mostly be between −10° and +20° C. The skilled in the art will easily be able to determine optimum conditions depending on the equipment used, the temperature of the hot aqueous APM solution and the type and amount of ketone.

The amount of ketone to be used depends on the type of ketone applied, and should effectively result in an open drainable network of APM crystals when the method of the present invention is performed. If the amount of ketone used is too small a "sherbet-like" pseudo solid phase will be obtained, or at best a crystal network having poor draining properties, that is, a network from which less than 30% of mother liquor can be drained by gravitational force only. If too much ketone is applied a 2-layer system, with all its inherent problems, will be formed. Preferably the ketone is used in such an amount that the solvent system is homogeneous.

The crystallizing system preferably is kept in a condition of low or negligible agitation or mechanical disturbance, allowing sufficient time for crystallization to take place.

The aqueous phase should preferably be kept without mechanical agitation or the like for an average time of at least 15 minutes after the system temperature has reached the nucleation temperature and crystallization is continued. During said residence time a kind of network of APM crystals is formed, which may be stronger or weaker depending on, among other things, the amount of aspartame present, but which, according to the present invention, can easily be drained so that at least 25% by wt. of the solvent is removed from the crystals by gravitational forces only; if necessary, the remaining crystal network after draining can easily be destroyed by mechanical treatment. In any event the network formed according to this method is different from a sherbet-like pseudo solid phase as formed in static crystallization: th  tter, when formed in a beaker, will retain all of the aqueous solvent when the beaker is turned upside-down.

As indicated above, the drained network may, after destruction of the network structure, optionally be cooled further by direct or indirect cooling. By such further cooling the yield of crystals obtained can be increased. This may be done either by further cooling the bottom part of the crystallizing equipment or by withdrawing crystal slurry therefrom to another vessel, cooled to a lower temperature in the range of 0°–20° C., and carrying out the further crystallization in said additional vessel. Preferably the further crystallization then is done while stirring because this increases the cooling rate and crystal output per unit of time. Remarkably, this higher yield of crystals is obtained without any adverse effect on crystal size and properties.

The mother liquor obtained from the first draining step can also be cooled further for recovering APM therefrom (but, of course, in that case the crystal properties of this second crystallization are less favourable); this APM, however, can then be redissolved and used again in the process of the invention for increasing the total crystallization yield.

After crystallization of APM and draining, optionally with further inert gas treatment, according to the invention, the APM crystal sludge obtained may be washed and, if desired, dried in the same vessel and any organic solvent remaining in the aqueous phase may be removed from it by a method known per se, such as evaporation.

The invention will now be further explained by means of the following experiments and comparative experiments, without, however, being restricted thereto.

Experiments and comparative experiments 1–22

A series of crystallization experiments (nos. 1–13) from various aqueous aspartame solutions in the presence of ketones was carried out in 200 ml beakers (diameter 5.8 cm;

glass) to test the drainability of the open networks obtained. In each of the experiments a warm, about 65° C., solvent mixture was prepared by adding a known amount of the chosen ketone to a known amount of demineralized water (or of a demineralized water/methanol mixture) which had already been heated to that temperature; immediately thereafter a predetermined amount of crystalline aspartame was added and dissolved in the solvent mixture with gentle stirring, and the beaker was covered with a plastic sheet to minimize the effects of solvent evaporation. The homogeneous solutions of aspartame thus obtained had compositions as shown in table 1. Crystallization from each of these solutions was performed by setting the beakers aside for one night in a conditioned room having a temperature of 21° C.

Drainability tests were then carried out as follows: after removal of the plastic cover sheet each of the beakers was placed under an angle of 30° with the horizontal plane, the opening of the beaker facing down, and mother liquor was allowed to drain from the crystalline mass obtained, whereby the beaker was turned around its central axis for about 90 degrees from time to time. After draining of mother liquid (M.L.) from the crystalline mass had substantially stopped, which usually occurred well within 30 minutes, the remaining crystal mass was weighed. The remaining crystal mass was then dried in an oven at 60° C. Drainability was calculated as a percentage by dividing the amount of drained M.L. by the total amount of M.L. removed by draining and solvent removed in the drying step. The results are shown in table 1.

For comparison also some experiments (comparative experiments 14–22) are shown which were performed in the same way but in which some of the conditions were varied, such as experiments without addition of ketone, or using an excessively high concentration of aspartame, or cooling to below 10° C. These experiments are also summarized in table 1. Since in these tests no draining was observed, no further measurements were performed.

Note: All experiments involved cooling to 21° C., except comparative experiments nos. 19–22, which involved cooling to 3° C.

In the table, "ac" means acetone, "MIBK" means methylisobutylketone, "MeOH" means methanol, and "IPA" means isopropylalcohol

TABLE 1

| Exp. No. | solvent | compn (g) | APM (g) | M.L. drained (g) | solvent removed drying (g) | drainability (%) | recovery yield APM[1] (%) |
|---|---|---|---|---|---|---|---|
| 1 | water | 180.62 | 7.99 | 125.20 | 63.80 | 66.24 | 80.43 |
|   | ac | 10.05 | | | | | |
| 2 | water | 166.82 | 8.02 | 155.30 | 29.10 | 84.22 | 77.54 |
|   | ac | 19.97 | | | | | |
| 3 | water | 158.22 | 8.00 | 165.20 | 20.30 | 89.06 | 73.85 |
|   | ac | 29.96 | | | | | |
| 4 | water | 177.64 | 12.00 | 76.80 | 109.50 | 41.22 | 92.42 |
|   | ac | 10.11 | | | | | |
| 5 | water | 158.04 | 12.02 | 142.40 | 42.80 | 76.89 | 84.51 |
|   | ac | 29.99 | | | | | |
| 6 | water | 150.24 | 11.99 | 116.10 | 68.10 | 63.03 | 87.31 |
|   | ac | 39.81 | | | | | |
| 7 | water | 191.75 | 8.28 | 148.57 | 41.34 | 78.23 | 74.48 |
|   | MIBK | 0.20 | | | | | |
| 8 | water | 191.45 | 8.28 | 147.97 | 41.86 | 77.95 | 79.11 |
|   | MIBK | 0.51 | | | | | |
| 9 | water | 190.95 | 5.28 | 158.60 | 32.13 | 83.15 | 76.23 |
|   | MIBK | 1.00 | | | | | |

TABLE 1-continued

| Exp. No. | solvent | compn (g) | APM (g) | M.L. drained (g) | solvent removed drying (g) | drainability (%) | recovery yield APM[1] (%) |
|---|---|---|---|---|---|---|---|
| 10 | water | 190.45 | 8.28 | 158.31 | 32.27 | 83.07 | 78.74 |
|    | MIBK | 1.50 | | | | | |
| 11 | water | 189.95 | 8.28 | 151.88 | 38.57 | 79.75 | 82.12 |
|    | MIBK | 2.00 | | | | | |
| 12 | water | 168.00 | 10.00 | 127.43 | 64.22 | 66.49 | 83.50 |
|    | MIBK | 2.00 | | | | | |
|    | MeOH | 20.00 | | | | | |
| 13 | water | 168.00 | 10.00 | 94.67 | 96.69 | 49.47 | 86.70 |
|    | MIBK | 2.00 | | | | | |
|    | IPA | 20.00 | | | | | |

Comparative Experiments:

| 14 | water | 185.22 | 7.99 | no draining | | | |
| 15 | water | 176.30 | 12.48 | no draining | | | |
|    | MeOH | 9.84 | | | | | |
| 16 | water | 126.44 | 12.21 | no draining | | | |
|    | ac | 14.05 | | | | | |
| 17 | water | 118.34 | 12.25 | no draining | | | |
|    | ac | 20.90 | | | | | |
| 18 | water | 108.44 | 12.21 | no draining | | | |
|    | ac | 27.94 | | | | | |
| 19 | water | 131.15 | 9.10 | no draining | | | |
|    | ac | 6.78 | | | | | |
| 20 | water | 122.15 | 9.00 | no draining | | | |
|    | ac | 14.04 | | | | | |
| 21 | water | 119.05 | 8.98 | no draining | | | |
|    | ac | 21.27 | | | | | |
| 22 | water | 113.75 | 8.97 | no draining | | | |
|    | ac | 28.24 | | | | | |

[1]this figure includes APM crystallized during drying

Experiment and comparative experiment 23/23A

A 2.5 liter beaker (diameter 14.4 cm; glass), provided with a possibility for bottom discharge through a 24 mm diameter opening positioned at the centre of the beaker and provided with a stopper was filled with a 65° C. solvent mixture of 2350 g of demineralized water and 25 g of MIBK, and 125 g of APM was dissolved therein with gentle stirring, and the beaker was covered with a plastic sheet to minimize the effects of solvent evaporation. Crystallization from this solution was performed by setting the beaker aside for one night at ambient temperature (21° C.), without agitation. Then the stopper was removed, and the mother liquor drained under gravitational force only was collected. The amount of mother liquor so obtained in about 30 minutes was 1656 g. There remained in the beaker an "open drainable network" wet crystal mass, occupying about the same volume as the original crystallizing system. A gentle flow of nitrogen, heated to about 65° C., was then blown top down through the crystal mass; the crystal mass was thus dried overnight, and a further 740 g of solvent was removed during that step. The draining percentage was 69.12%. The product thus obtained had a very short dissolution time[2] of less than 3 minutes for 99% of the crystals. Almost no time was required for wetting the product.

[2] Dissolution time was determined for the products of this experiment and the comparative experiment by an indirect method, namely by conductivity measurement. 200 ml of demineralized water was charged into a 250 ml vessel, thermostatted at 20° C., and 1.40 g of APM was added thereto while stirring with a 40 mm magnetic stirrer at 700 rpm. The conductivity was measured using a Lauda type Pt80 probe and a Philips 9510/65 cell (cell constant 1.0). Although the absolute values of conductivity may vary depending on the level of ionic impurities in the sample, this method provides an easy, indirect way of determining dissolution times. 99% of dissolution corresponds to 99% of the ultimate change in conductivity.

In contrast, when the same experiment was performed (23A) in the absence of MIBK, only very little draining, less than 10%, was observed, and drying could not be achieved in the same apparatus. The total dissolution time according to the same dissolution test was much longer, about 6 minutes for 99%.

In addition, the electrostatic behaviour of the dried products obtained in experiments 23 and 23A was tested by the so-called "spoon-test". In this test 30 g of APM (preconditioned for 24 hours at 20° C. and 30% relative humidity) is charged into a plastic bag of polyethylene film. A clean stainless steel spoon is introduced into the bag and the APM is stirred for 10 seconds. Then the spoon is withdrawn, filled with powder, whereafter the contents of the spoon are discharged again into the bag by gently shaking the spoon for 5 seconds. The amount of APM still adhering to the spoon is determined gravimetrically, and the spoon is cleaned. This test is repeated a number of times.

The average amount of APM adhering to the spoon was found to be 9.1±3.8 mg for the product of experiment 23, and 21.5±5.9 for the product of experiment 23A. This is a very significant and surprising difference.

Experiment 24

Two 1.0 liter beakers (diameter 9.0 cm; glass) were filled with a 65° C. solvent mixture of 752 g of demineralized water and 8 g of MIBK; 40 g of APM was dissolved therein with gentle stirring, and the beakers were covered with a plastic sheet to minimize the effects of solvent evaporation. Crystallization from this solution was performed by setting the beakers aside for one night at 22° C. in a conditioned room without agitation. The "open drainable network" crystal masses thus obtained were broken and formed into a slurry by gentle stirring with a spoon for 5 minutes at 22° C. The slurry from the first beaker was used to determine the specific cake resistance of the crystals obtained by the leaf-test method at $\Delta p=0.1$ bar and at 22° C. this was found to be $4.27*10^7$ m/kg. The slurry from the second beaker was cooled further to 10° C. in a vessel with stirring in about one hour, and the specific cake resistance of the crystals obtained after said further cooling step was found to be $7.0*10^7$ m/kg at $\Delta p=0.1$ bar and 10° C. thus crystals remain of excellent quality in terms of specific cake resistance upon further cooling.

Experiment and comparative experiment 25/25A 7510 g of a 65° C. APM solution (clear and homogeneous) was prepared which had the following composition: 7058 g of demineralized water, 75 g of MIBK and 377 g of APM. This solution was divided into 3 portions of about 2.5 liters each, which were charged into 2.5 liter beakers (diameter 14.4 cm; glass). The beakers were covered with a plastic sheet to minimize the effects of solvent evaporation. Crystallization from this solution was performing by leaving the beakers, without agitation, for one night at 22° C. in a conditioned room. The "open drainable network" crystal masses thus obtained were broken and formed into a slurry by gentle stirring with a spoon for 5 minutes at 22° C. These slurries were tested for their filtration behaviour on a 0.01 m² Büchner funnel at $\Delta p=0.5$ bar and in a centrifuge (type: CEPA; diameter: 20 cm; height: 11 cm; rotational speed 2677 rpm for 5 minutes), respectively. For comparison purposes the same experiment was also carried out in the absence of MIBK, other things being equal (25A).

It was observed that by the Büchner filtration method solvent could be removed from the slurries obtained in this experiment and the comparative experiments to a wet cake moisture content of 74.3 and 70%, respectively. That is, slightly better for the slurries obtained without MIBK.

A surprising and significant difference in favour of the method of the invention, however, was found for the centrifuge tests: the wet cake after centrifuging the product obtained using MIBK had a moisture content of 24%, whereas the wet cake obtained without using MIBK was found to have a moisture content of 31%. Thus, the product of the method according to the invention is very suitable for being centrifuged; this leads to effective savings in washing and further drying.

What we claim is:

1. A method for crystallizing α-L-aspartyl-L-phenylalanine methyl ester comprising conductive cooling an aqueous solution of α-L-aspartyl-L-phenylalanine methyl ester while avoiding turbulence in the crystallizing system being formed during said conductive cooling, wherein said aqueous solution to be conductively cooled has a temperature of at least about 40° C. and contains from about 2.5 to 7% by weight of α-L-aspartyl-L-phenylalanine methyl ester and is cooled to a temperature level not lower than 10° C. in the presence of at least 0.1% by weight of a ketone selected from the group of $C_{3-8}$ ketones, the amount of ketone and the temperature level being selected for each individual ketone so that a homogeneous solvent system is present at the start of crystallization and an open drainable network of α-L-aspartyl-L-phenylalanine methyl ester and mother liquor is obtained.

2. A method according to claim 1 wherein the method comprises the further step of removing at least 30% by weight of the mother liquor present after crystallization by gravitational force from the open drainable network of α-L-aspartyl-L-phenylalanine methyl ester crystals and mother liquor.

3. A method of crystallizing α-L-aspartyl-L-phenylalanine methyl ester by crystallizing α-L-aspartyl-L-phenylalanine methyl ester by conductive cooling an aqueous solution of α-L-aspartyl-L-phenylalanine methyl ester whereby a crystallizing system is formed by said cooling, while avoiding turbulence in said crystallizing system, wherein said aqueous solution being subjected to conductive cooling has an initial temperature of at least 40° C. and contains from 2.5 to 7% by weight of α-L-aspartyl-L-phenylalanine methyl ester, said aqueous solution being cooled to a temperature level not lower than 10° C. in the presence of at least 0.1% by weight of a ketone selected from the group of $C_{3-6}$ ketones, the amount of ketone and the temperature level being selected for each individual ketone so that a homogeneous solvent system is present at the start of crystallization and an open drainable network of α-L-aspartyl-L-phenylalanine methyl ester crystals is obtained which contains mother liquor;

removing at least 30% by weight of the mother liquor present after crystallization by gravitational force from the open drainable network of α-L-aspartyl-L-phenylalanine methyl ester crystals; and additionally passing an inert gas through the resulting α-L-aspartyl-L-phenylalanine crystal structure.

4. A method according to claim 3 wherein the inert gas additionally has an elevated temperature in the range of 60°–100° C., and the inert gas is passed through the resulting α-L-aspartyl-L-phenylalanine crystal structure.

5. A method according to any one of claims 3 and 4 wherein passing the inert gas is carried out under reduced pressure.

6. A method according to claim 1, 2, 4, or 3 wherein the pH of the aqueous solution is in the range of 3.5 to 6.5.

7. A method according to claim 1, 2, 4, or 3, wherein said conductive cooling takes place until a temperature in the range of 15° to 30° C. is reached.

8. A method according to claim 1, 2, 4 or 3, wherein the conductive cooling is carried out for at least 15 minutes after crystallization has started.

9. A method according to claim 1, 2, 4 or 3, wherein the ketone is selected from the group consisting of 2-propanone, 2-butanone, methyl-isobutylketone and 2,5-hexanedione.

10. A method according to claim 9, wherein the ketone is acetone in an amount of about 1.0 to 20.0% by weight or methyl-isobutylketone in an amount of 0.1 to 2.0% by weight.

11. A method according to any one of claims 1, 2, 4 or 5, wherein at least 0.1% of the ketone by weight is added to the crystallization system before crystallization starts.

12. A method according to any one of claims 2 or 3, wherein the network obtained after at least 30% by weight of the mother liquid has been drained is cooled further to a temperature in a range of 0° C. to 30° C.

13. A method according to claim 1 wherein the mother liquor is cooled for recovering additional α-L-aspartyl-L-phenylalanine methyl ester by crystallization and the aspartame crystals thereby obtained from the mother liquor are recycled to a solution to be used in a process of claim 1.

14. A method according to claim 3 wherein the removed mother liquor is cooled for recovering additional α-L-aspartyl-L-phenylalanine methyl ester by crystallization and the aspartame crystals thereby obtained from the mother liquor are recycled to a solution to be used in a process of claim 14.

15. A method according to claim 5 wherein the pH of the aqueous solution is in the range of 3.5 to 6.5.

16. A method according to claim 6, wherein the pH of the aqueous solution is about 5.2.

17. A method according to claim 5, wherein the pH is about 5.2.

18. A method of crystallizing α-L-aspartyl-L-phenylalanine methyl ester which consists essentially of the steps of:

providing an aqueous solution of α-L-aspartyl-L-phenylalanine methyl ester, wherein said aqueous solution has a temperature of at least 40° C., contains from 2.5 to 7% by weight of α-L-aspartyl-L-phenylalanine methyl ester, and contains at least 0.1% by weight of a ketone selected from the group of $C_{3-6}$ ketones, wherein the amount of ketone and the temperature level are selected based on each individual ketone so that a homogeneous solvent system is obtained; and crystallizing α-L-aspartyl-L-phenylalanine methyl ester by conductive cooling said aqueous solution of α-L-aspartyl-L-phenylalanine methyl ester to a temperature level of not lower than 10° C. whereby a crystallization system is obtained, wherein turbulence in said crystallization system is avoided during said conductive cooling and crystals of α-L-aspartyl-L-phenylalanine methyl ester crystals are formed in said crystallization system.

* * * * *